DEFENSIVE PUBLICATION

UNITED STATES PATENT AND TRADEMARK OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent and Trademark Office makes no assertion as to the novelty of the disclosed subject matter.

PUBLISHED MARCH 2, 1976

944 O.G. 42

T944,010

POLYMERIZATION PROCESS WHEREIN POLYMERS ARE PRODUCED FROM SATURATED ALIPHATIC HYDROCARBONS EMPLOYING A COMBINATION OF A STRONG LEWIS ACID AND A STRONG BRONSTED ACID

Durward T. Roberts, Jr., and Joseph A. Beckman, Akron, Lawrence E. Calihan, Cuyahoga Falls, and Adel F. Halasa, Bath, Ohio, assignors to The Firestone Tire & Rubber Company, Akron, Ohio

Continuation of application Ser. No. 368,563, June 11, 1973, which is a continuation-in-part of application Ser. No. 191,814, Oct. 22, 1971, both now abandoned. This application Dec. 24, 1974, Ser. No. 536,121

Int. Cl. C07c *9/00, 11/00*

U.S. Cl. 260—676 R

No Drawing. 15 Pages Specification

Polymers, including dimers, trimers, oligomers and higher polymers are produced from saturated aliphatic hydrocarbon monomer of from 1 to 20 carbon atoms. The monomer is contacted with a mixture of a strong Lewis acid and a strong Bronsted acid at a temperature of from —80° to 120° C. The combination of a strong Lewis acid and a strong Bronsted acid acts to produce alkylcarbonium ions from saturated aliphatic hydrocarbons, under the selective reaction conditions, add and produce polymeric chains. The strong Lewis acid is one which has a relatively greater ability to accept an electron pair. The Lewis acids which are most useful in the invention comprise halides of metals from Groups IIIA to VIIA of the Periodic Chart, although atoms outside these groups can be present as well. The Bronsted acids which are effective in the method of the invention are those which most readily give up a proton. The strong, Bronsted acids in the inventions include the following; HF, $HSO_3F$, $HSO_3CF_3$, $HPO_3F$, HCl, $HSO_3Cl$, $HClO_4$ and $H_2SO_4$. The amount of acid combination present can be as high as one mole of total acid per mole of monomer,